US012779076B2

(12) United States Patent
Hsiao

(10) Patent No.: US 12,779,076 B2
(45) Date of Patent: Nov. 3, 2026

(54) SCENT WARMER

(71) Applicant: DONGGUAN YIH TEH ELECTRIC PRODUCTS CO., LTD., DongGuan City (CN)

(72) Inventor: Ming Jen Hsiao, Miaoli County (TW)

(73) Assignee: DONGGUAN YIH TEH ELECTRIC PRODUCTS CO., LTD., Dongguan City (CN)

(*) Notice: Subject to any disclaimer, the term of this patent is extended or adjusted under 35 U.S.C. 154(b) by 293 days.

(21) Appl. No.: 18/767,313

(22) Filed: Jul. 9, 2024

(65) Prior Publication Data

US 2026/0014289 A1 Jan. 15, 2026

(51) Int. Cl.

| | |
|---|---|
| ***A61L 9/03*** | (2006.01) |
| ***F21S 10/04*** | (2006.01) |
| ***F21V 3/02*** | (2006.01) |
| *F21Y 113/00* | (2016.01) |
| *F21Y 115/10* | (2016.01) |

(52) U.S. Cl.

CPC ................ *A61L 9/03* (2013.01); *F21S 10/04* (2013.01); *F21V 3/02* (2013.01); *A61L 2209/11* (2013.01); *A61L 2209/12* (2013.01); *A61L 2209/135* (2013.01); *F21Y 2113/00* (2013.01); *F21Y 2115/10* (2016.08)

(58) Field of Classification Search

CPC .............. A61L 9/03; F21S 10/04; F21V 3/02

See application file for complete search history.

(56) References Cited

U.S. PATENT DOCUMENTS

| | | | |
|---|---|---|---|
| 8,066,420 | B2 | 11/2011 | Hsiao |
| 8,201,957 | B2 | 6/2012 | Hsiao |
| 8,765,073 | B1 | 7/2014 | Hsiao |
| 8,787,739 | B2 | 7/2014 | Hsiao |
| 8,938,159 | B2 | 1/2015 | Hsiao |
| 8,974,107 | B2 | 3/2015 | Hsiao |
| 8,983,277 | B2 | 3/2015 | Hsiao |
| 9,031,392 | B2 | 5/2015 | Hsiao |
| 9,109,780 | B2 | 8/2015 | Hsiao |
| 9,206,963 | B2 | 12/2015 | Hsiao |
| 9,410,695 | B2 | 8/2016 | Hsiao |
| 9,500,358 | B2 | 11/2016 | Hsiao |
| 10,046,969 | B2 | 8/2018 | Shibuya et al. |
| 10,842,901 | B2 | 11/2020 | Hsiao |

(Continued)

*Primary Examiner* — Kevin Joyner

(74) *Attorney, Agent, or Firm* — HDLS IPR SERVICES; Chun-Ming Shih

(57) ABSTRACT

A scent warmer, includes a heater for generating electric heat to a heat conductor to heat the fragrance in the inner container of the scent warmer to produce fragrance; and a lighting device integrated in a housing. The lighting device has a candle-like lamp protruding from the upper side of the housing to produce a candle-like light effect, which does not produce chaotic smoke and open flames, and is safe and environmentally friendly. The lighting device includes a first lighting unit that emits light onto a light-transmissive safety lampshade, forming a light effect that shines inside and outside the housing, creating a light decorative effect, enhancing the ambient atmosphere for using the fragrance diffuser, and having a lighting effect, so that the evaporation of the fragrance substance of the scent warmer inside the housing and the amount of the fragrance substance stored can be observed.

19 Claims, 6 Drawing Sheets

(56) References Cited

U.S. PATENT DOCUMENTS

| | | | | |
|---|---|---|---|---|
| 11,045,570 | B2 | 6/2021 | Hsiao | |
| 11,421,840 | B1 | 8/2022 | Hsiao | |
| 11,421,850 | B1 | 8/2022 | Hsiao | |
| 2010/0096376 | A1 | 4/2010 | Hsiao | |
| 2014/0126892 | A1 | 5/2014 | Hsiao | |
| 2015/0109823 | A1 | 4/2015 | Hsiao | |
| 2015/0117056 | A1 | 4/2015 | Hsiao | |
| 2016/0195257 | A1 | 7/2016 | Hsiao | |
| 2018/0126022 | A1 | 5/2018 | Hsiao | |
| 2020/0222571 | A1 | 7/2020 | Hsiao | |
| 2021/0247042 | A1 * | 8/2021 | Wu ......................... | F21S 6/001 |

* cited by examiner

SCENT WARMER

BACKGROUND OF THE INVENTION

1. Field of the Invention

The present invention relates to a scent warmer, and in particular to a scent warmer that can produce a candle-like light ambience effect.

2. Description of the Related Art

The reason that users favor over the combination of candle light colors and aroma is due to the scent from aromatic candles, the lighting effect produce by candle lights and the atmosphere created by aromatic lightings. However, a candle's lighting effect could be affected by the airflow around and produce smokes. Furthermore; candle could produce pollutions such as PM 2.5 and encounter the danger of burning completely.

A conventional aroma lamp candle heater can use an incandescent light bulb to emit light and to heat the aromatic substance above the lampshade to release a scent and to provide a certain atmosphere in the room.

However, the lamp from a conventional aroma diffuser with a lamp commonly uses an incandescent light bulb that has a low heating efficiency, and furthermore, there is a heating distance in between the light bulb and the aromatic substance, so the decreasing heat conduction leads to inefficient heating of the aromatic substance. Further, the lighting unit is an incandescent light bulb, which is not being designed in accordance with the eco-friendly regulations; further, the incandescent light bulb from said aroma heater has a low lighting efficiency, therefore the lighting performance of said aroma heater is unsatisfied; further, conventional lamp of said aroma heater without a light-transmissive safety lampshade cover over the electric power conduction component, user can reach easily, and the electric power conduction and light bulb safety could easily be threatening, such as U.S. Pat. Nos. 8,201,957B2 and 8,066,420B2.

SUMMARY OF THE INVENTION

In view of the above-mentioned problems in the prior art, the present invention provides a scent warmer that can produce a candle-like light ambience effect. The heat source of the scent warmer quickly and evenly heats the aromatic substances in the scent warmer, effectively producing fragrance. Combined with the candle-like light, it creates a fragrance and light effect atmosphere. The candle-like light does not produce chaotic smoke or open flames, and is safe and environmentally friendly.

The present invention provides a scent warmer, wherein the light emitted by the light emitting element of the lighting device is projected onto a light-transmissive safety lampshade, and the produced light effects in the scent warmer can enhance the ambient atmosphere of the fragrance diffuser and produce lighting effects, so that the evaporation of the aromatic substances inside the scent warmer and the amount of aromatic substances stored can be observed.

The present invention provides a scent warmer, which can effectively dissipate the fragrance generated by a fragrance diffusion port, and the high temperature generated by the heater can be dissipated through the fragrance diffusion port to prevent the high temperature from affecting the performance of the lighting device and its control circuit, and the large-diameter window of the fragrance diffusion port allows you to more clearly observe the evaporation of the aromatic substances inside the scent warmer and the amount of aromatic substances stored.

The present invention provides a scent warmer, which uses a light-emitting element of a lamp that complies with environmental safety regulations and utilizes a sturdy safety lampshade to seal and protect the light-emitting element and circuit to avoid electric shock hazards.

In some embodiment of the present invention providing a scent warmer, comprising a lighting device, a connecting member, a fixing ring, a heat conductor, a heater, a base, a power source connection unit, and a housing.

The lighting device comprising a light-transmissive safety lampshade, a control circuit, a candle-like lamp, and a first lighting unit.

The light-transmissive safety lampshade comprises a lower opening on the lower side and a light-transmissive lower shell. The control circuit and the first lighting unit are arranged in the light-transmissive safety lampshade. The light-transmissive lower shell is coupled to the lower opening. The candle-like lamp protrudes out of the light-transmissive safety lampshade. The candle-like lamp and the first lighting unit are electrically coupled to the control circuit.

The connecting member has one side thereof connected to the lighting device, and an opposite side thereof connected to the fixing ring.

The heat conductor is coupled to the fixing ring.

The heater, the heater is coupled to the lower side of the heat conductor and is located inside the fixing ring.

The base comprises a first opening and a chamber extending inward from the first opening. The fixing ring, the heat conductor and the heater on the other side of the connecting member are combined in the first opening.

The power source connection unit is electrically connected to the heater and the control circuit.

The housing comprises a second opening on the upper side and a third opening on the lower side. The housing is detachably connected to the first opening of the base from the third opening, and covers the lighting device and the connecting member. The candle-like lamp at least partially protrudes from the second opening.

The power source connection unit is used to electrically connect a power source to the control circuit of the lighting device and the heater, so that the heat source generated when the heater is powered on can quickly and evenly heat the aromatic substance in the scent warmer, effectively producing the aroma. When the lighting device is powered on, the candle-like lamp protruding from the second opening on the upper side of the housing generates a candle-like light, which complements the candle-like light generated by the candle-like lamp to form a fragrance and lighting atmosphere effect. The candle-like light will not produce chaotic smoke and open flames, which is safe and environmentally friendly. The light emitted by the first lighting unit is projected onto the light-transmissive safety lampshade, generating a light effect in the scent warmer to enhance the ambient light effect atmosphere of the diffuser. With lighting effect, you can observe the evaporation of the aromatic substances inside the scent warmer and the amount of aromatic substances stored.

According to some embodiments of the scent warmer of the present invention, the lighting device forms a candle light effect in the scent warmer of the present invention, and generates a lighting atmosphere effect and lighting use in the scent warmer. The scent warmer of the present invention combines the function of diffusing fragrance and the flame effect of simulating candle lights. Compared with the commonly used scented candles, the scent warmer of the present invention has no open flame and will not produce smoke pollution. The lack of open flame can also avoid the problem of fire hazards.

The first lighting unit has lighting and light effect atmosphere functions, and can be used alone or in combination with the candle-like lamp and the heater to heat the aromatic substance to produce fragrance, thereby solving the problems of the fragrance diffusion effect and light effect of the conventional lamp candle heat diffusers or scented candles.

In some embodiments of the scent warmer of the present invention, when making a comparison with conventional products, the light device that is designed according to eco-friendly regulations with a lighting unit such as LED chip that replaces lighting from traditional incandescent light bulbs and a heater with a desirable heating function.

In some embodiments of the present invention, the scent warmer can produce a lighting effect that follows eco-friendly regulations, and a heater with a desirable heating function can replace a poor heating result from the traditional incandescent light bulb to heat aromatic substances and produce scent stably. The scent warmer of the present invention can produce a lighting effect and also follow eco-friendly regulations, and the heater can replace the incandescent light bulb to heat aromatic substances, the heater of the scent warmer has a greater heating function to heat aromatic substance from a container to effectively heat an aromatic substance and to produce scent stably, especially a container with large amount of aromatic substance.

In some embodiments of the scent warmer of the present invention, the lighting unit is designed according to eco-friendly regulations to replace traditional incandescent light bulbs and to use the light-transmissive safety lampshade to seal the electronic components and lighting unit within the lampshade by sturdy material to avoid breaking the lampshade and to protect the lighting unit and the electric circuit within the lampshade, the light-transmissive safety lampshade can avoid the children and others break the lampshade and become exposed under the threat of being in contact with electricity. In the present invention, the scent warmer provide the heating source to heat the aromatic substance to produce scent, and to combine candle-like light, and at the same time to produce different lighting colors, the scent warmer can produce a better scent with lighting effect and atmosphere.

DETAILED DESCRIPTION OF THE PREFERRED EMBODIMENT

Figure 1:
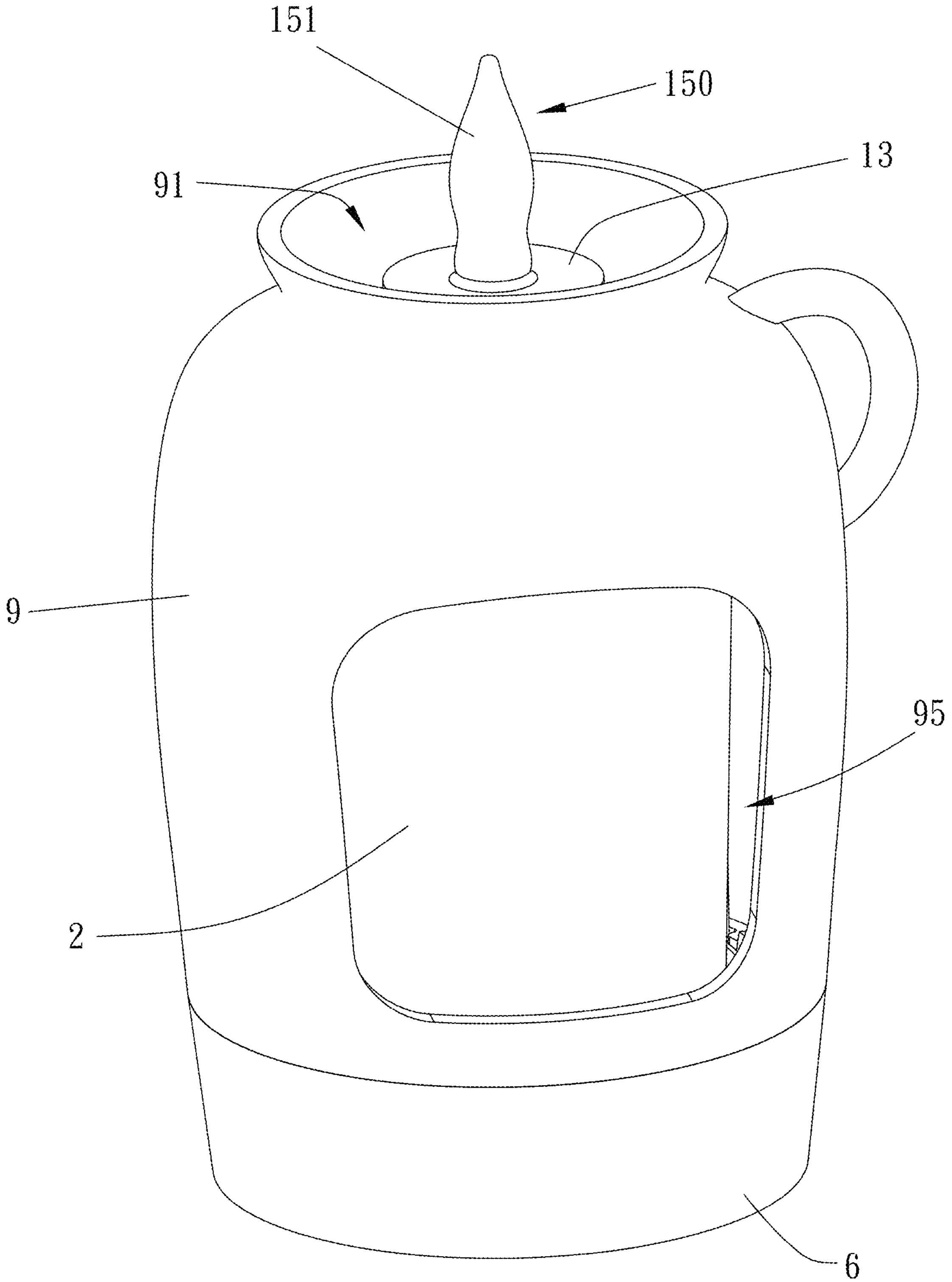
FIG. 1 is a perspective view of the Scent warmer of the present invention.

Referring to FIGS. 1-4, a scent warmer according to an embodiment of the present invention comprises a lighting device 1, a connecting member 3, a fixing ring 37, a heat conductor 4, a heater 5, a base 6, a power source connection unit 65, and a housing 9.

The lighting device 1 comprising a light-transmissive safety lampshade 13, a control circuit 15, a candle-like lamp 150, and a first lighting unit 153.

The light-transmissive safety lampshade 13 comprises a lower opening 131 on the lower side and a light-transmissive lower shell 132. The control circuit 15 and the first lighting unit 153 are arranged in the light-transmissive safety lampshade 13. The light-transmissive lower shell 132 is coupled to the lower opening 131. The candle-like lamp 150 protrudes out of the light-transmissive safety lampshade 13. The candle-like lamp 150 and the first lighting unit 153 are electrically coupled to the control circuit 15.

The connecting member 3 has one side thereof connected to the lighting device 1, and an opposite side thereof connected to the fixing ring 37.

The heat conductor 4 is coupled to the fixing ring 37.

The heater 5, the heater 5 is coupled to the lower side of the heat conductor 5 and is located inside the fixing ring 37.

The base 6 comprises a first opening 61 and a chamber 63 extending inward from the first opening 61. The fixing ring 37, the heat conductor 4 and the heater 5 on the other side of the connecting member 3 are combined in the first opening 61.

The power source connection unit 65 is electrically connected to the heater 5 and the control circuit 15.

The housing 9 comprises a second opening 91 on the upper side and a third opening 93 on the lower side. The housing 9 is detachably connected to the first opening 61 of the base 6 from the third opening 93, and covers the lighting device 1 and the connecting member 3. The candle-like lamp 150 at least partially protrudes from the second opening 91.

The power source connection unit 65 is used to electrically connect a power source to the control circuit 15 of the lighting device 1 and the heater 5, so that the heat source generated when the heater 5 is powered on can quickly and evenly heat the aromatic substance in the scent warmer, effectively producing the aroma. When the lighting device 1 is powered on, the candle-like lamp protruding from the second opening 91 on the upper side of the housing 9 generates a candle-like light, which complements the candle-like light generated by the candle-like lamp to form a fragrance and lighting atmosphere effect. The candle-like light will not produce chaotic smoke and open flames, which is safe and environmentally friendly. The light emitted by the first lighting unit 153 is projected onto the light-transmissive safety lampshade, generating a light effect in the scent warmer to enhance the ambient light effect atmosphere of the diffuser. With lighting effect, you can observe the evaporation of the aromatic substances inside the scent warmer and the amount of aromatic substances stored.

According to some embodiments of the scent warmer of the present invention, the lighting device forms a candle light effect in the scent warmer of the present invention, and generates a lighting atmosphere effect and lighting use in the scent warmer. The scent warmer of the present invention combines the function of diffusing fragrance and the flame effect of simulating candle lights. Compared with the commonly used scented candles, the scent warmer of the present invention has no open flame and will not produce smoke pollution. The lack of open flame can also avoid the problem of fire hazards.

The first lighting unit 153 has lighting and light effect atmosphere functions, and can be used alone or in combination with the candle-like lamp 151 and the heater 5 to heat the aromatic substance to produce fragrance, thereby solving the problems of the fragrance diffusion effect and light effect of the conventional lamp candle heat diffusers or scented candles.

Referring to FIGS. 1-4, the candle-like lamp 150 comprises a candle flame-shaped light-transmitting lampshade 151 and a second lighting unit 152. The second lighting unit 152 is electrically connected to the control circuit 15. The candle flame-shaped light-transmitting lampshade 151 protrudes from the upper side of the light-transmissive safety lampshade 13. The second lighting unit 152 is integrated into the candle flame-shaped light-transmitting lampshade 151.

In some embodiments of the scent warmer of the present invention, the lighting device 1 that is designed according to eco-friendly regulations with the heater 5. The first lighting unit 153 and the second lighting unit 152 such as LED chip that replaces a traditional incandescent light bulb to resolve the problem of limited lighting efficiency and the control circuit 15 contains a LED circuit and electrically couples with a converter 155. The power source connection unit 65 connects with a power source such as power source in 120V to the control circuit 15, the converter 155, to convert the 120V power source within the operation of LED chip, such as 30 mA and lower the electric pressure from 2.9 V to 3.0 V (in every LED chip).

LED includes any candle light color such as red, yellow, orange, orange-red, orange-yellow and other color changes. The second lighting unit LED 152 is used to generate a candle-like color reflection on the candle flame-shaped light-transmitting lampshade 151, thereby generating a candle flame shape effect and a candle light color light effect atmosphere. The first lighting unit 153 can emit light of various colors to project onto the light-transmissive safety lampshade to produce light effects and lighting effects.

The LED includes any one of MCU LED, RGB LED or color LED, which is used to produce various candle light color changes or candle light flashing effects. The housing 9 is a light-transmitting housing, and the candle flame-shaped light-transmitting lampshade 151 is a light-transmitting lampshade. The power source connection unit 65 is connected to the control circuit 15 to provide the first lighting unit 153 with various light color changes, which are reflected inside and outside the light-transmitting housing 9 to generate light color atmosphere and lighting, or/and provide the second lighting unit 152 to generate simulated candle light on the candle flame-shaped light-transmitting lampshade 151, forming simulated candle light effect on the scent warmer. The light emitting diode (LED) includes any color of red, yellow, orange, orange-red, orange-yellow, white, blue, or green.

The built-in microcontroller (MCU) in LED lamps can realize functions such as brightness adjustment, color change, remote control, energy-saving mode and scene setting, making LED more applicable and improving energy efficiency.

In some embodiments, the written code is uploaded to the MCU (e.g., using Arduino IDE, AVR Studio IDE). After the code is uploaded, the MCU can control the brightness of the LED light. You can see the LED flashing once at a predetermined interval to produce a candle light flashing effect, or the light switches once to change the light color.

The housing 9 is a light-transmitting housing, whereby the power source connection unit 65 connects power supply to the control circuit 15, so as to provide the first lighting unit 153 with various light color changes, which are reflected inside and outside the light-transmitting housing 9, generating light color atmosphere and lighting, or/and provide the second lighting unit 152 to generate simulated candle light on the candle flame-shaped light-transmitting lampshade 151, forming simulated candle light effect on the scent warmer.

The light-transmitting housing 9 includes, for example, any one of light-transmitting ceramics, light-transmitting plastics or light-transmitting acrylic. The material of the light-transmissive safety lampshade 13 includes any of the following materials that are not easy to break: light-transmissive plastic, semi-transmissive plastic, light-transmissive or semi-transmissive acrylic. The light-transmissive safety lampshade 13 seals the control circuit 15, the second lighting unit 152 and the first lighting unit 153, thereby preventing the hot aroma of the aromatic substance from damaging the control circuit 15 and the light-emitting element, and preventing the user or children from touching the circuit board and causing the danger of electric shock, which is safer.

Referring to FIGS. 2-5, according to some embodiments of the present invention, the connecting member further comprises a first hollow frame 31, a second hollow frame 33, and a fixing frame 35. The fixing frame 35 is coupled between the upper side of the first hollow frame 31 and the upper side of the second hollow frame 33. The bottom side of the light-transmissive safety lampshade 13 is covered on the fixing frame 35. The light-transmissive lower shell 132 covers the lower side of the fixing frame 35. The fixing ring 37 is coupled between the first hollow frame 31 and the lower side of the second hollow frame 33. The power source connection unit 65 passes through the chamber 63 and the first hollow frame 31 or the second hollow frame 33 to the light-transmissive safety lampshade 13 to electrically connect to the control circuit 15, thereby providing power to the candle-like lamp 150 and the first lighting unit 153.

The first hollow frame 31 and the second hollow frame 33 are connected to each other by forming a sharp angle with respect to the central axis of the fixing frame 35, the heat conductor 4 and the fixing ring 37. Thus, an open state is formed between the first hollow frame 31 and the second hollow frame 33 on both sides of the heat conductor 4, relative to one side of the sharp angle, so that the container 2 containing aromatic substances can be detachably placed on or detached from the heat conductor 4 by passing between the first hollow frame 31 and the second hollow frame 33.

Referring to FIGS. 2-5, according to some embodiments of the present invention, the heat conductor 4 is a circular metal heat conducting sheet with a rod 43 extending from its lower side; the heater 5 is a circular structure with a first hole 51 formed in the middle thereof. The heater 5 is connected to the lower side of the heat conductor 4 by penetrating the rod 43 through the first hole 51. The user can thereby separate the housing 9 from the base 6 and place a container 2 containing an aromatic substance, such as a wax cup filled with a large amount of aromatic wax, between the first hollow frame 31 and the second hollow frame 33 in an open state, and easily and conveniently place the wax cup on the heat conductor 4. The circular heater 5 provides a large amount of even heat to the circular heat conductor 4, and the heat source will not be concentrated in the center of the container 2 (wax cup). The heat conductor 4 can evenly and quickly heat the wax cup and the large amount of scented wax inside, which can quickly and effectively produce fragrance, and the scented wax in the wax cup can be completely heated and evaporated without waste. Wherein the heater 5 includes either a cement resistor or a PTC.

Referring to FIGS. 2-5, according to some embodiments of the present invention, an inner step 66 is formed inside the chamber 63 of the base 6, and the connecting member 3 is coupled to the inner step 66 via the fixing ring 37. The opening 61 of the base 6 is formed with a convex wall 67, and the convex wall 67 is arranged around the outer edge of the inner step 66. The housing 9 is detachably mounted on the outer side of the convex wall 67 through the second opening 91 and is coupled to the first opening 61 of the base 6. Thereby, the user can conveniently and quickly detach or assemble the housing 9 from the base 6 so as to replace the container 2 containing the aromatic substance on the heat conductor 4.

Referring to FIGS. 2-5, according to some embodiments of the present invention, the scent warmer further comprises a heating insulation unit 39, which is disposed between the fixing ring 37 and the heat conductor 4, and surrounds the outer periphery of the circular heater 5. The heating insulation unit 39 is used to isolate the heat source of the heat conductor 4 and the heater 5 from being transmitted to the base 6, so as to prevent the heat source from being transmitted to the desktop where the scent warmer is placed.

Wherein the heating insulation unit 39 is either a ring-shaped structure or a plurality of sheet-shaped structures.

Wherein the material of the heating insulation unit 7 comprises any of a silicon, a mica sheet, a break lining sheet or an asbestos plate.

Figure 2:
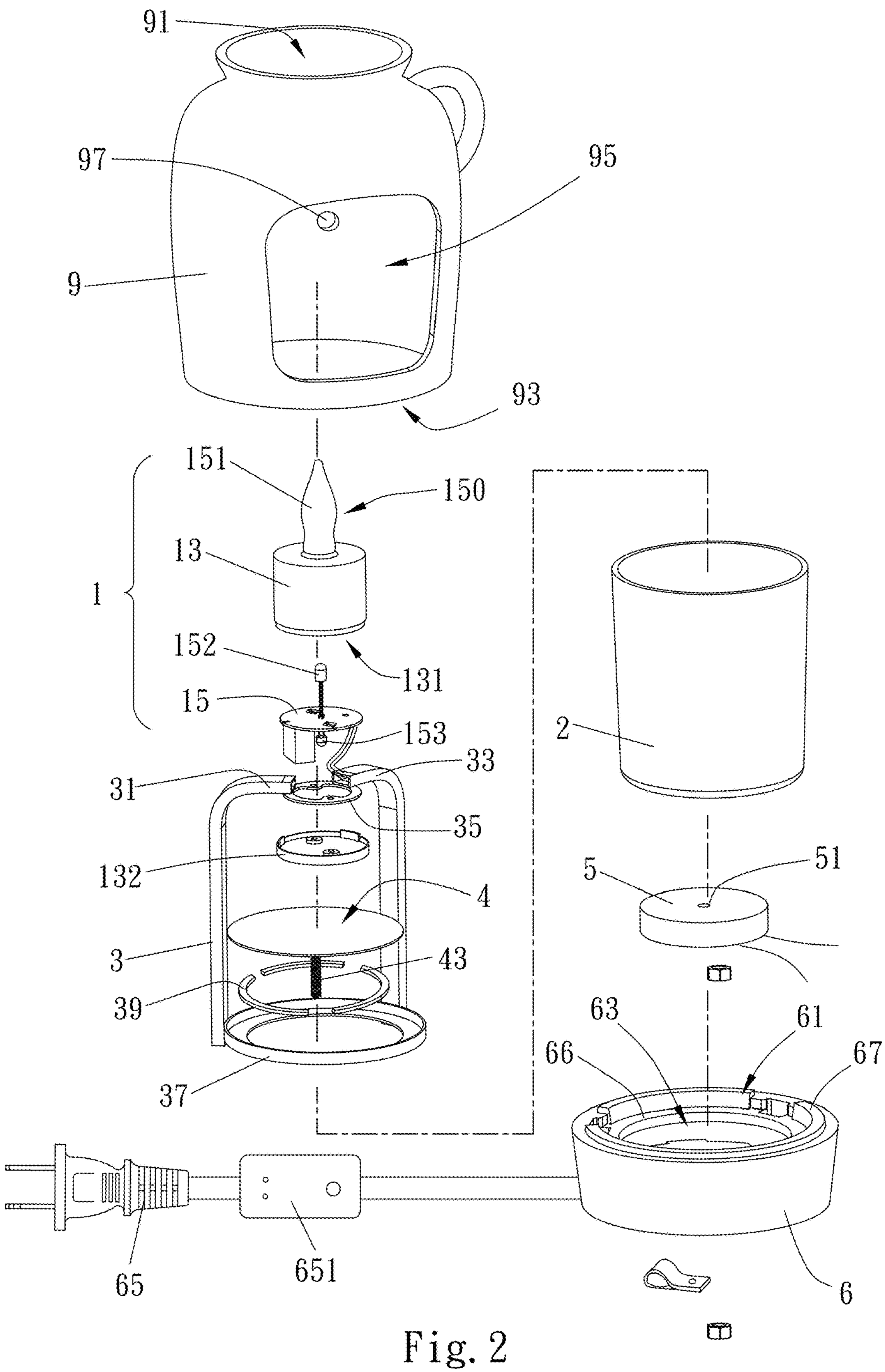
FIG. 2 is an exploded view of the Scent warmer of the present invention.
Figure 3:
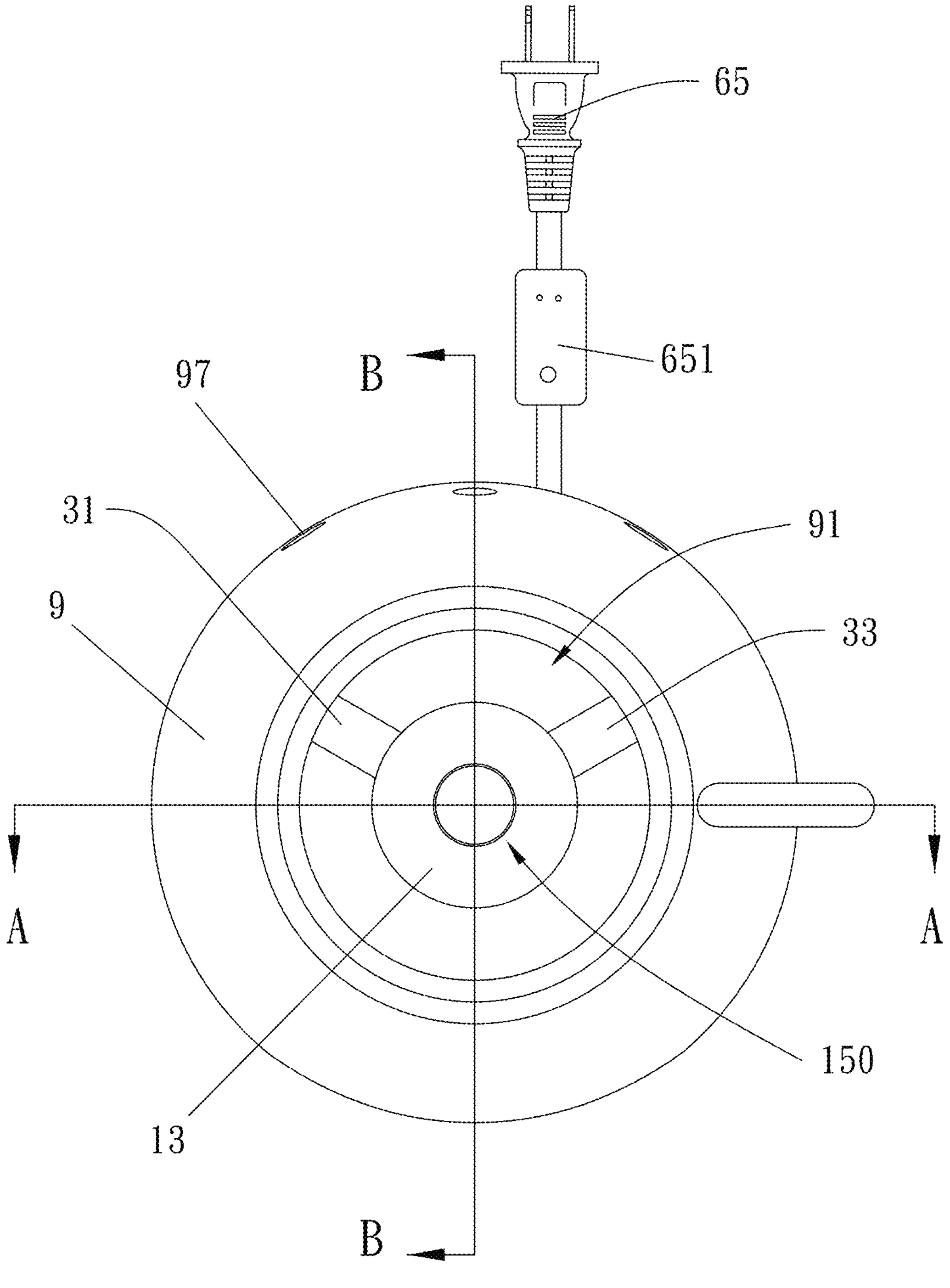
FIG. 3 is a top view of the Scent warmer of the present invention of FIG. 1.
Figure 4:
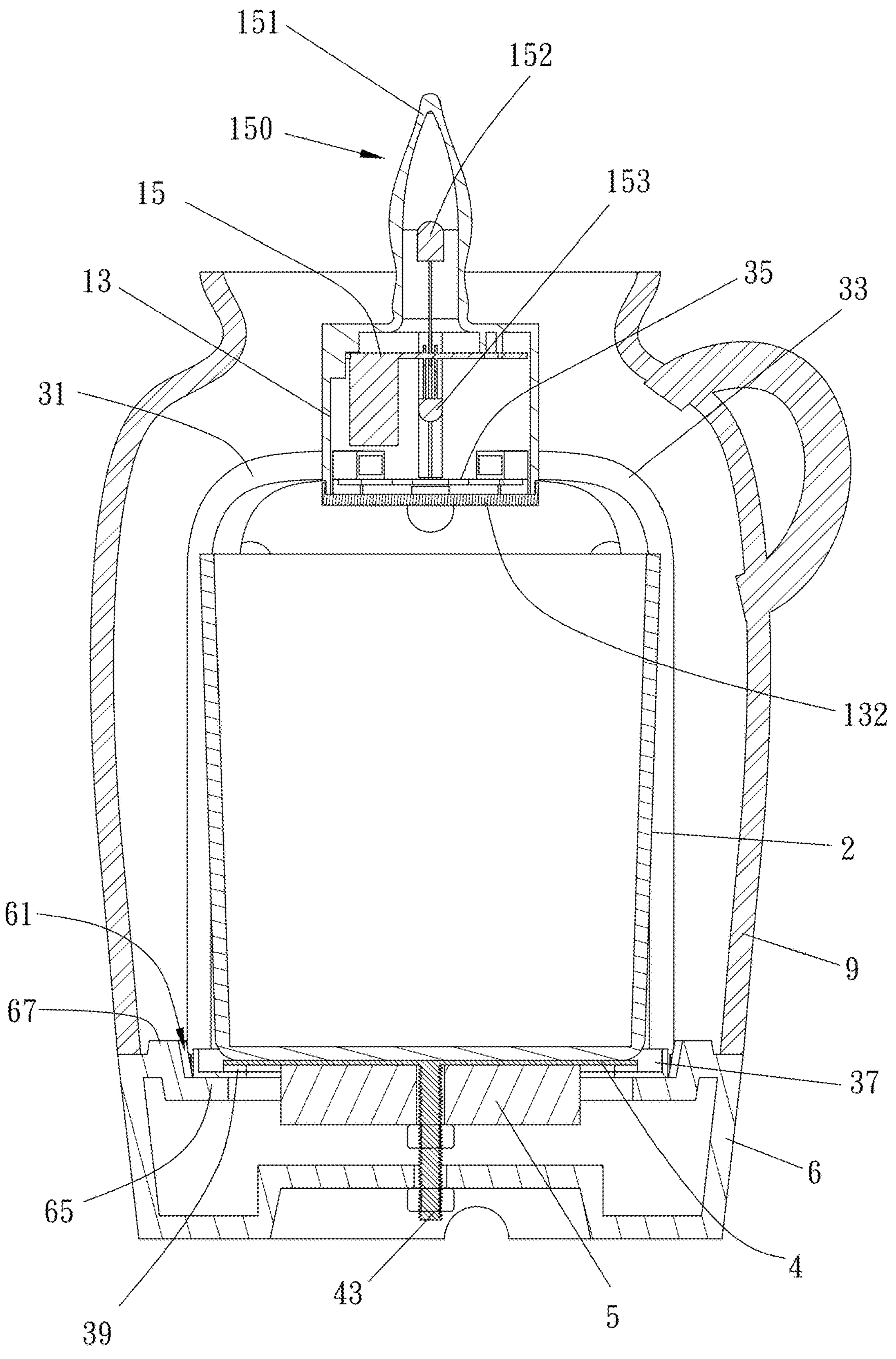
FIG. 4 is a cross-sectional side view of the Scent warmer of the present invention in FIG. 3 along line segment A-A.
Figure 5:
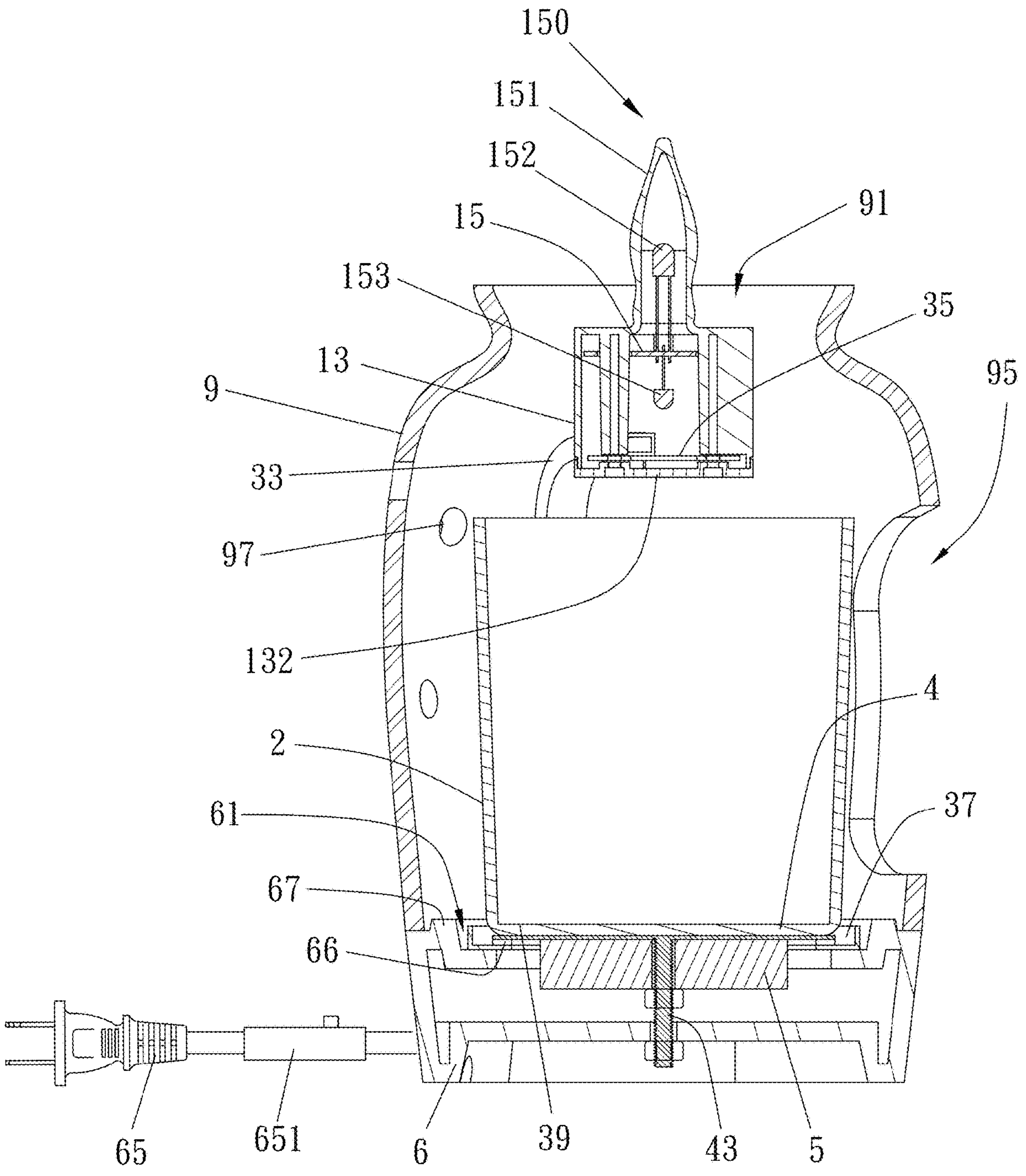
FIG. 5 is a cross-sectional side view along line B-B in FIG. 3.

Referring to FIGS. 1, 2 and 5, according to some embodiments of the present invention, the housing 9 further comprises a fragrance diffusion port 95. The fragrance diffusion port 95 is opened on one side of the housing 9 and has a large hole structure. The fragrance and heat inside the scent warmer can be quickly dissipated to the outside, which can enhance the fragrance and heat dissipation effect of the scent warmer, and at the same time, the use of the aromatic substances inside the housing 9 can be observed.

The housing 9 further comprises a plurality of second holes 97, and the second holes 97 are connected to the fragrance diffusion port 95, so as to achieve better convection, fragrance diffusion and heat dissipation effects of the hot air generated by the heater 5 inside the housing 9.

Referring to FIGS. 1, 2, 5, in some embodiments of the scent warmer of the present invention, the control circuit 15 controls the first lighting unit 153 LED chip to present different variations of lighting effects including color variations. The light emitted is projected onto the light-transmissive safety lampshade 13 to produce various light effects, which are used to form various color-changing light effects in the scent warmer and comply with environmental safety regulations. The heater 5 has a greater heating function to heat an aromatic substance at a container 2, to effectively heat the aromatic substance and to produce scent stably, especially a container with large amount of aromatic substance.

Figure 6:
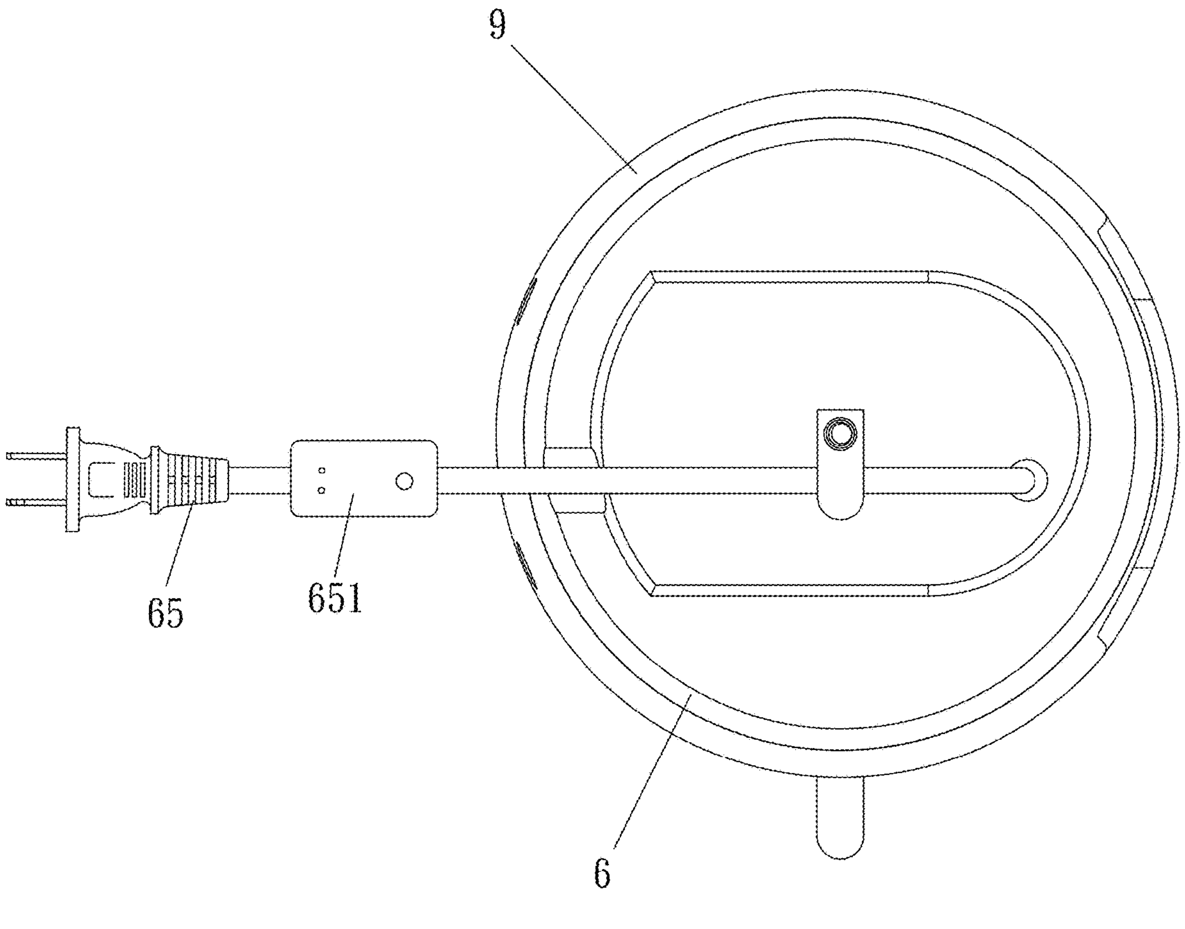
FIG. 6 is a bottom view of FIG. 1.

Referring to FIGS. 2, 5 and 6, according to some embodiments of the present invention, the power source connection unit 65 comprises a control switch 651 provided on a power line. The control switch 651 has two switching positions: position one (large wax pot mode): the cement resistor works at 35 W power for 2 hours, then reduces to 20 W for continuous operation; position two (medium wax pot mode): the cement resistor works at 35 W power for 1 hour, then reduces to 20 W for another 1 hour, then reduces to 13 W for continuous operation.

In some embodiments of the present invention, aromatic substance such as essential oil, aromatic wax, spice or aromatic balm, etc. In some embodiments, the aromatic substance of the present invention use cement resistor to heat and can stably improve heating efficiency and replace the problem of producing insufficient temperature to be heated by conventional incandescent light bulbs.

The above descriptions are only some embodiments of the present invention, the invention should not be limited by the scope of the new embodiments, this means the modifications and enhancements of the claims and the embodiments may be made without departing from the spirit and scope of the invention.

What the invention claimed is:

1. A scent warmer, comprising:

a lighting device comprising a light-transmissive safety lampshade, a control circuit, a candle-like lamp and a first lighting unit, said light-transmissive safety lampshade comprising a lower opening and a light-transmissive lower shell, said control circuit and said first lighting unit being arranged in said light-transmissive safety lampshade, said light-transmissive lower shell being combined with said lower opening, said candle-like lamp protruding from said light-transmissive safety lampshade, said candle-like lamp and said first lighting unit being electrically coupled to said control circuit;

a connecting member having one side thereof coupled to said lighting device and an opposite side thereof coupled to a fixing ring;

a heat conductor coupled to said fixing ring;

a heater coupled to a lower side of said heat conductor and located inside said fixing ring;

a base comprising a first opening and a chamber opened inwardly from said first opening, said first opening being provided for said fixing ring, said heat conductor and said heater to be combined in said first opening;

a power source connection unit electrically connected to said heater and said control circuit respectively; and a housing, said housing comprising a second opening on an upper side thereof and a third opening on an opposing lower side thereof, said housing being detachably connected to said first opening of said base from said third opening to cover said lighting device and said connecting member so that said candle-like lamp at least partially protrudes from said second opening.

2. The scent warmer as claimed in claim 1, wherein said candle-like lamp comprises a candle flame-shaped light-transmitting lampshade and a second lighting unit, said second lighting unit being electrically connected to said control circuit, said candle flame-shaped light-transmitting lampshade protruding from an upper side of said light-transmissive safety lampshade, said second lighting unit being incorporated into said candle flame-shaped light-transmitting lampshade.

3. The scent warmer as claimed in claim 2, wherein said second lighting unit and said first lighting unit are light emitting diodes (LEDs), and said control circuit further comprises an LED driving circuit device.

4. The scent warmer as claimed in claim 3, wherein said light emitting diodes (LEDs) comprises MCU LEDs, RGB LEDs, or color LEDs.

5. The scent warmer as claimed in claim 3, wherein said light emitting diodes (LEDs) comprises any color of red, yellow, orange, orange-red, orange-yellow, white, blue, or green.

6. The scent warmer as claimed in claim 3, wherein said housing is a light-transmitting housing.

7. The scent warmer as claimed in claim 1, wherein the material of said light-transmissive safety lampshade comprises light-transmissive plastic, half light-transmissive plastic, light-transmissive acrylic, or half light-transmissive acrylic from any of the sturdy material.

8. The scent warmer as claimed in claim 1, wherein said connecting member comprises a first hollow frame, a second hollow frame and a fixing frame, said fixing frame being connected between an upper side of said first hollow frame and an upper side of said second hollow frame, said light-transmissive safety lampshade covering said fixing frame with a bottom side thereof, said light-transmissive lower shell covering a lower side of said fixing frame, said fixing ring being connected between said first hollow frame and a lower side of said second hollow frame, said power source connection unit passed through said chamber and through one of said first hollow frame and said second hollow frame and being electrically connected to said control circuit in said light-transmissive safety lampshade.

9. The scent warmer as claimed in claim 8, wherein said first hollow frame and said second hollow frame are connected to each other by forming a sharp angle with respect to the central axis of said fixing frame, said heat conductor and said fixing ring, thereby an open state is formed between said first hollow frame and said second hollow frame on both sides of said heat conductor, on one side relative to the sharp angle, so that a container filled with aromatic substances is able to be conveniently placed on or detached from said heat conductor by passing between said first hollow frame and said second hollow frame.

10. The scent warmer as claimed in claim 9, wherein said heat conductor is a circular metal heat conducting sheet with a rod extending from a lower side thereof; said heater corresponds to a circular structure with a first hole formed in the middle thereof, said heater being connected to a lower side of said heat conductor by penetrating said rod through said first hole.

11. The scent warmer as claimed in claim 10, wherein said heater is selectively a cement resistor or a PTC.

12. The scent warmer as claimed in claim 10, wherein said chamber of said base has an inner step formed therein, and said connecting member is coupled to said inner step via said fixing ring.

13. The scent warmer as claimed in claim 12, wherein said opening of said base forms a convex wall, said convex wall surrounding an outer edge of said inner step; said housing is detachably mounted on an outer side of said convex wall via said second opening and is coupled to said first opening of said base.

14. The scent warmer as claimed in claim 10, further comprising a heating insulation unit, said heating insulation unit being arranged between said fixing ring and said heat conductor, and surrounding the outer periphery of said circular heater.

15. The scent warmer as claimed in claim 14, wherein said heating insulation unit is a ring-shaped structure or a multiple lamellar structure.

16. The scent warmer as claimed in claim 14, wherein the material of said heating insulation unit comprises silicon sheet, mica sheet, break lining sheet or asbestos plate.

17. The scent warmer as claimed in claim 1, wherein said housing further comprises a fragrance diffusion port, said fragrance diffusion port being opened on one side of said housing, said fragrance diffusion port being used to enhance the fragrance diffusion and heat dissipation effects of the scent warmer, and at the same time for allowing the user to observe the usage of aromatic substances inside said housing.

18. The scent warmer as claimed in claim 17, wherein said housing further comprises a plurality of second holes, said second holes being connected to said fragrance diffusion port for convection and heat dissipation of the hot air generated by said heater inside said housing.

19. The scent warmer as claimed in claim 1, wherein said power source connection unit comprises a power line with a control switch.

* * * * *